(12) United States Patent
Ternes et al.

(10) Patent No.: US 8,805,502 B2
(45) Date of Patent: Aug. 12, 2014

(54) MANAGING CROSS THERAPY DELIVERY IN A MULTIPLE THERAPY IMPLANTABLE DEVICE

(71) Applicant: Cardiac Pacemakers, Inc., St. Paul, MN (US)

(72) Inventors: David J. Ternes, Roseville, MN (US); Stephen Ruble, Lino Lakes, MN (US); Jeffrey E. Stahmann, Ramsey, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/705,430

(22) Filed: Dec. 5, 2012

(65) Prior Publication Data

US 2013/0165985 A1 Jun. 27, 2013

Related U.S. Application Data

(60) Provisional application No. 61/580,419, filed on Dec. 27, 2011.

(51) Int. Cl.
*A61N 1/00* (2006.01)
*A61N 1/36* (2006.01)
*A61N 1/362* (2006.01)
*A61N 1/37* (2006.01)

(52) U.S. Cl.
CPC ............ *A61N 1/36114* (2013.01); *A61N 1/362* (2013.01); *A61N 1/3704* (2013.01); *A61N 1/36* (2013.01)
USPC ................................................ 607/9; 607/18

(58) Field of Classification Search
CPC ... A61N 1/36114; A61N 1/362; A61N 1/372; A61N 1/36; A61N 1/3704; A61N 1/3605; A61N 1/3962
USPC ............ 607/9, 11, 14, 17–19, 27–28, 27–8, 2
See application file for complete search history.

(56) References Cited

U.S. PATENT DOCUMENTS

| 5,203,326 A | 4/1993 | Collins |
| 6,169,918 B1 | 1/2001 | Haefner et al. |

(Continued)

FOREIGN PATENT DOCUMENTS

| WO | WO-2010051475 A1 | 5/2010 |
| WO | WO-2013101409 A1 | 7/2013 |

OTHER PUBLICATIONS

"International Application Serial No. PCT/US2012/067860, International Search Report mailed Apr. 2, 2013", 4 pgs.

(Continued)

*Primary Examiner* — Catherine Voorhees
(74) *Attorney, Agent, or Firm* — Schwegman, Lundberg & Woessner, P.A.

(57) ABSTRACT

An apparatus comprises a cardiac signal sensing circuit configured to sense an electrical cardiac signal from at least one of an atrium or ventricle of a heart of a subject, a therapy circuit configured to provide electrical pacing therapy and electrical neural stimulation therapy to the subject, and a control circuit. The control circuit is configured to initiate delivery of the electrical pacing therapy, initiate a blanking period in a time relationship to the delivery of electrical pacing therapy, and initiate delivery of the electrical neural stimulation therapy to the subject during the blanking period. At least one sense amplifier of the cardiac signal sensing circuit is disabled during the blanking period.

8 Claims, 15 Drawing Sheets

(56) References Cited

U.S. PATENT DOCUMENTS

| | | | |
|---|---|---|---|
| 7,493,161 B2 | 2/2009 | Libbus et al. | |
| 7,881,782 B2 | 2/2011 | Libbus et al. | |
| 8,000,793 B2 | 8/2011 | Libbus | |
| 8,478,404 B2* | 7/2013 | Maile et al. | 607/9 |
| 2005/0149132 A1 | 7/2005 | Libbus | |
| 2005/0149133 A1* | 7/2005 | Libbus et al. | 607/9 |
| 2005/0245976 A1* | 11/2005 | Wang | 607/9 |
| 2006/0206154 A1* | 9/2006 | Moffitt et al. | 607/9 |
| 2008/0021507 A1* | 1/2008 | Libbus et al. | 607/17 |
| 2008/0103532 A1 | 5/2008 | Armstrong et al. | |
| 2008/0228238 A1 | 9/2008 | Libbus | |
| 2008/0269819 A1* | 10/2008 | Zhou | 607/14 |
| 2009/0234408 A1* | 9/2009 | Moffitt et al. | 607/14 |
| 2010/0114199 A1* | 5/2010 | Krause et al. | 607/4 |
| 2010/0185255 A1 | 7/2010 | Libbus | |
| 2010/0191307 A1 | 7/2010 | Fang et al. | |
| 2010/0228317 A1 | 9/2010 | Libbus et al. | |
| 2010/0274321 A1 | 10/2010 | Libbus | |
| 2010/0286740 A1 | 11/2010 | Libbus et al. | |
| 2010/0305634 A1 | 12/2010 | Moffitt et al. | |
| 2010/0318154 A1 | 12/2010 | Libbus et al. | |
| 2011/0015690 A1 | 1/2011 | Ryu et al. | |
| 2011/0082514 A1 | 4/2011 | Libbus et al. | |
| 2011/0082537 A1 | 4/2011 | Moffitt et al. | |
| 2011/0105926 A1* | 5/2011 | Kornet et al. | 600/510 |
| 2011/0106216 A1 | 5/2011 | Libbus et al. | |
| 2011/0112592 A1 | 5/2011 | Libbus et al. | |
| 2011/0118802 A1 | 5/2011 | Usui | |
| 2011/0137360 A1 | 6/2011 | Ternes | |
| 2011/0190840 A1 | 8/2011 | Shuros et al. | |
| 2013/0138170 A1* | 5/2013 | Ternes et al. | 607/18 |

OTHER PUBLICATIONS

"International Application Serial No. PCT/US2012/067860, Written Opinion mailed Apr. 2, 2013", 7 pgs.

* cited by examiner

US 8,805,502 B2

MANAGING CROSS THERAPY DELIVERY IN A MULTIPLE THERAPY IMPLANTABLE DEVICE

CLAIM OF PRIORITY

This application claims the benefit of priority under 35 U.S.C. §119(e) of Ternes et al., U.S. Provisional Patent Application Ser. No. 61/580,419, filed on Dec. 27, 2011, the benefit of priority of which is claimed hereby, and is incorporated by reference herein in its entirety.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

Implanted cardiac stimulators have been used to deliver medical therapies. Examples of cardiac stimulators include pacemakers, implantable cardiac defibrillators (ICDs), and implantable devices capable of performing pacing and defibrillating functions.

OVERVIEW

This document relates generally to systems, devices, and methods that provide electrical neural stimulation therapy to a patient or subject. In particular it relates to systems, devices, and methods that deliver electrical neural stimulation therapy and electrical pacing therapy.

An apparatus example can include a cardiac signal sensing circuit configured to sense an electrical cardiac signal from at least one of an atrium or ventricle of a heart of a subject, a therapy circuit configured to provide electrical pacing therapy and electrical neural stimulation therapy to the subject, and a control circuit. The control circuit can be configured to initiate delivery of the electrical pacing therapy, initiate a blanking period in a time relationship to the delivery of electrical pacing therapy, and initiate delivery of the electrical neural stimulation therapy to the subject during the blanking period. At least one sense amplifier of the cardiac signal sensing circuit can be disabled during the blanking period.

This section is intended to provide an overview of subject matter of the present patent application. It is not intended to provide an exclusive or exhaustive explanation of the invention. The detailed description is included to provide further information about the present patent application.

DETAILED DESCRIPTION

Figure 1:
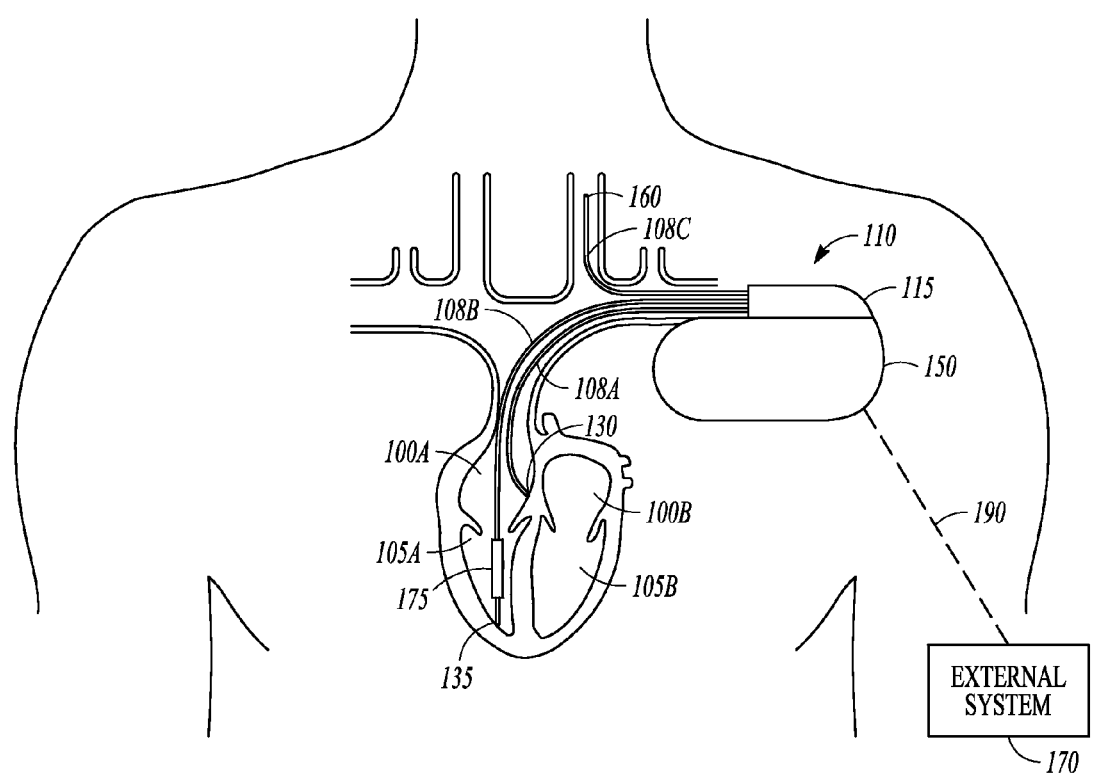
FIG. 1 is an illustration of an example of portions of a system that uses an IMD.

This document discusses systems and methods for delivering both electrical neural stimulation and electrical pacing therapy. A medical device can include one or more of the features, structures, methods, or combinations thereof described herein. For example, a neural stimulator may be implemented to include one or more of the advantageous features or processes described below. Such a device may be implemented to provide a variety of therapeutic or diagnostic functions.

Neural Stimulation Therapy (NST) can include autonomic modulation therapy (AMT). AMT involves the stimulation of the autonomic nervous system. For example, electrical stimulation of neural targets within the autonomic nervous system may be used to deliver AMT.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases using AMT to stimulate nerves and thereby modulate autonomic tone. Neural stimulation to treat cardiovascular diseases can be referred to as neurocardiac therapy (NCT). Vagal stimulation used to treat cardiovascular diseases may be termed either vagal stimulation therapy (VST) or NCT. However, VST may be delivered for non-cardiovascular diseases, and NCT may be delivered by stimulating a nerve other than the vagal nerve. Both VST and NCT are examples of AMT.

NCT, by way of example and not limitation, includes the stimulation of an autonomic neural target to provide a therapy for a cardiac arrhythmia, ischemia, heart failure, angina, atherosclerosis, blood pressure, and the like. By way of example and not limitation, autonomic neural targets used to deliver NCT include the vagus nerve, cardiac branches of the vagal nerves, the carotid sinus nerve, baroreceptors such as baroreceptors in the carotid sinus or baroreceptors in the pulmonary artery, chemoreceptors, cardiac fat pads, the spinal column or some nerve roots extending from the spinal column. Examples of cardiovascular diseases or conditions include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle may ensue which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

FIG. 1 is an illustration of an example of portions of a system that uses an IMD 110. In the example shown, the system provides a combination of NST (e.g., AMT) and cardiac function management (CFM). The IMD 110 may include one or more leads 108C to provide the NST. The neural stimulation lead 108C is designed for placement to provide therapy to specific areas of the nervous system and includes one or more electrodes 160. Electrodes of the lead can be positioned in blood vessel proximate to a nerve trunk or nerve bundle so that electrical stimulation passes through a vessel wall to stimulate the nerve. For instance, neural stimulation lead 108C may be positioned in the jugular vein.

Other placements involve positioning a neural stimulation lead near the carotid artery sheath. The carotid sheath is fibrous connective tissue that surrounds a vascular compartment in the neck containing the jugular vein and the carotid artery. These electrode configurations may be useful for placement proximal the vagus nerve. Descriptions of systems and methods to provide baroreflex stimulation can be found in U.S. Pat. No. 8,000,793, by Libbus et al., filed May 23, 2008, and entitled "Automatic Baroreflex Modulation Based on Cardiac Activity," which is incorporated herein by reference in its entirety.

The IMD 110 may deliver intermittent neural stimulation. For example, intermittent neural stimulation may be delivered to treat chronic diseases such as heart failure and hypertension. Intermittent neural stimulation can be delivered using a duty cycle of a stimulation period. Each duty cycle can include a train of neural stimulation pulses. The duty cycle and stimulation period need not be constant throughout the Neural Stimulation Therapy (NST). For example, the duration or frequency of the duty cycle can be adjusted to adjust an intensity of the NST. Also, the start and/or stop of the duty cycle can be dependent on enabling conditions. The duty cycle and/or stimulation period can be adjusted in every subsequent stimulation period. Unless expressly disclosed otherwise herein, "stimulation period" and "duty cycle" are not intended to only encompass constant values that result in neural stimulation in a precise periodic manner, but rather is intended to include intermittent neural stimulation where therapeutically-effective or prophylactically-effective neural stimulation is delivered for a time and then not delivered for a time, and then delivered for a time. In electrical stimulation, for example, a train of neural stimulation pulses (current or voltage) can be delivered during a duty cycle of stimulation.

The IMD 110 also provides CFM which can include one or more of cardiac pacing therapy, cardioversion or defibrillation therapy, and cardiac resynchronization therapy (CRT). The system can also include an IMD programmer or other external system 170 that communicates wireless signals 190 with the IMD 110, such as by using radio frequency (RF) signals, inductive signals, or other telemetry signals. The external system 170 can include an external device that communicates with a remote system via a network, such as a computer network or cellular phone network. In some examples, the remote system provides patient management functions and may include one or more servers to perform the functions.

The IMD 110 can include one or more cardiac leads 108A-B to couple the IMD to the heart. Cardiac leads 108A-B can include a proximal end that is coupled to IMD 110 and a distal end, coupled by electrical contacts or "electrodes" to one or more portions of a heart. The electrodes are configured to deliver cardioversion, defibrillation, pacing, or resynchronization therapy, or combinations thereof to at least one chamber of the heart. The electrodes can be electrically coupled to sense amplifiers to sense electrical cardiac signals. Sometimes the sensing circuits and electrodes are referred to as channels. For example, circuitry used to sense signals in an atrium is referred to as an atrial sensing channel, and circuitry used to sense signals in a ventricle is referred to as a ventricular sensing channel. When direction is taken into account due to position of one or more sensing electrodes, the sensing channel can be referred to as a sensing vector. The sensing circuits may include software or firmware to provide device-based logic to initiate and detect sensed signals.

Sensed electrical cardiac signals can be sampled to create an electrogram (sometimes called an egram). An electrogram can be analyzed by the IMD and/or can be stored in the IMD and later communicated to the external device 170 where the sampled signals can be displayed for analysis.

The illustration of the heart includes a right atrium 100A, a left atrium 100B, a right ventricle 105A, and a left ventricle 105B. Right atrial (RA) lead 108A includes electrodes (electrical contacts, such as ring electrode (not shown) and tip electrode 130) disposed in an atrium 100A of the heart for sensing signals, or delivering pacing therapy, or both, to the atrium 100A.

Right ventricular (RV) lead 108B includes one or more electrodes, such as a tip electrode and a ring electrode, for sensing signals, delivering pacing therapy, or both sensing signals and delivering pacing therapy. RV lead 108B optionally also includes additional electrodes, such as RV coil electrode 175 for delivering atrial cardioversion, atrial defibrillation, ventricular cardioversion, ventricular defibrillation, or combinations thereof to the heart. These electrodes may have larger surface areas than pacing electrodes, such as the tip and ring electrodes, in order to handle the larger energies involved in defibrillation.

High energy shock therapy can be delivered using the RV coil electrode 175 and an electrode formed on the hermetically-sealed IMD housing or can 150. In some examples, the shock therapy is delivered using the RV coil electrode 175 and a second defibrillation coil electrode (not shown) located proximal to the RV coil electrode 175 and configured (e.g., shaped and sized) for placement in the superior vena cava (SVC). In some examples, the SVC coil electrode and the can electrode are electrically tied together to improve defibrillation by delivering current from the RV coil electrode 175 more uniformly over the ventricular myocardium.

RV lead 108B optionally provides resynchronization therapy to the heart 105. Resynchronization therapy is typically delivered to the ventricles in order to better synchronize the timing of depolarization between ventricles. Resynchronization therapy can be delivered with or without an accompanying LV lead (not shown).

Figure 2:
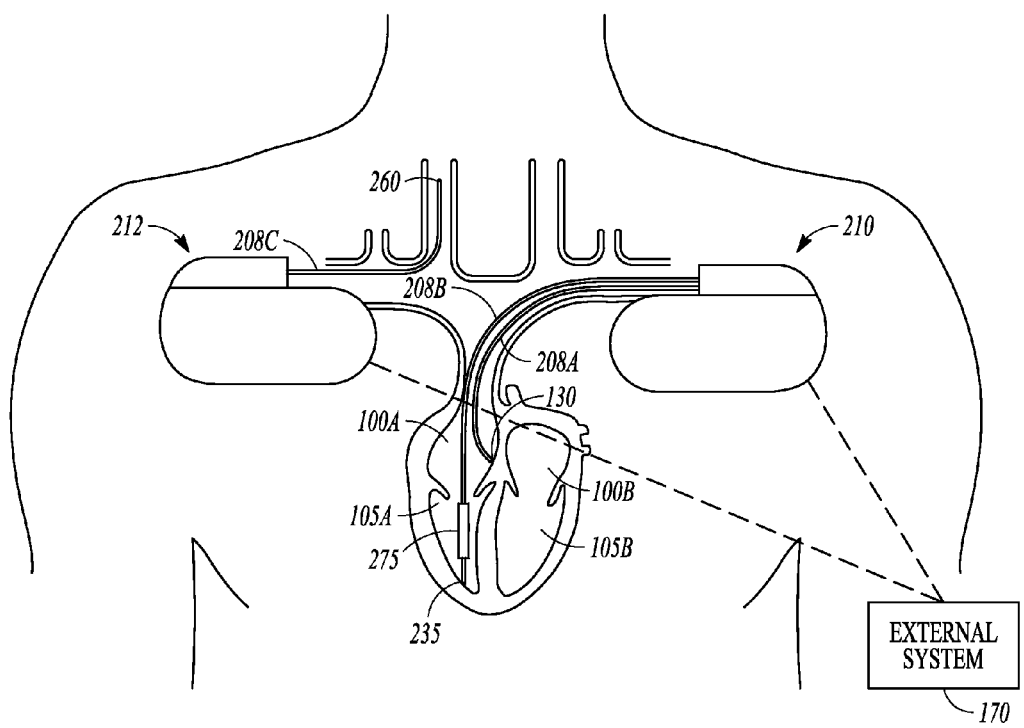
FIG. 2 is an illustration of an example of portions of a system that uses multiple IMDs.

FIG. 2 is an illustration of an example of portions of a system that uses two IMDs. Separate IMDs are used to provide the neural stimulation therapy and the cardiac stimulation therapy. The first IMD 210 provides CFM through sensing cardiac signals and providing cardiac therapy using cardiac leads 208A and 208B, and using electrodes 235, 275. The second IMD 212 is coupled to neural stimulation lead 208C and provides NST to the subject, using one or more electrodes 260. The external device 170 communicates wireless signals with the two IMDs to perform functions such as setting device parameters and collecting data. In some examples, the two IMDs communicate wirelessly with each other.

Figure 3:
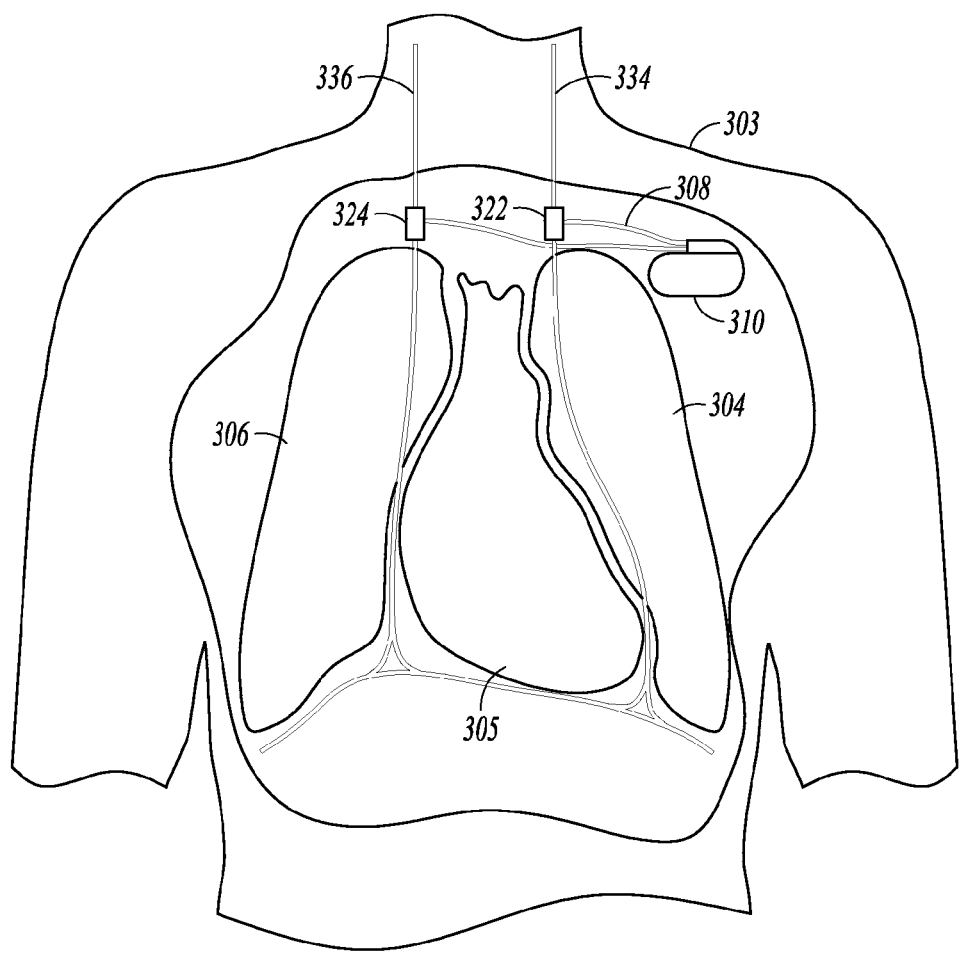
FIG. 3 is an illustration of an example of an IMD implanted in a thorax region of a patient.

Cuff electrodes may be used to stimulate nerve trunks. FIG. 3 is an illustration of another example of an IMD 310 implanted in a thorax region of a patient 303. The illustration shows the heart 305 of the subject as well as the left lung 304 and right lung 306. Also shown are representations of the left phrenic nerve 334 and right phrenic nerve 336. The IMD 310 is shown implanted in the pectoral region of the patient 303. In the example, the IMD 210 is coupled to one or more subcutaneous leads 208. The lead 308 can include one or more over-the-nerve cuffs 322 and 324 or collars containing electrodes for contacting a phrenic nerve. Cuff electrodes can also be used to contact and stimulate the vagus nerve.

Figure 4:
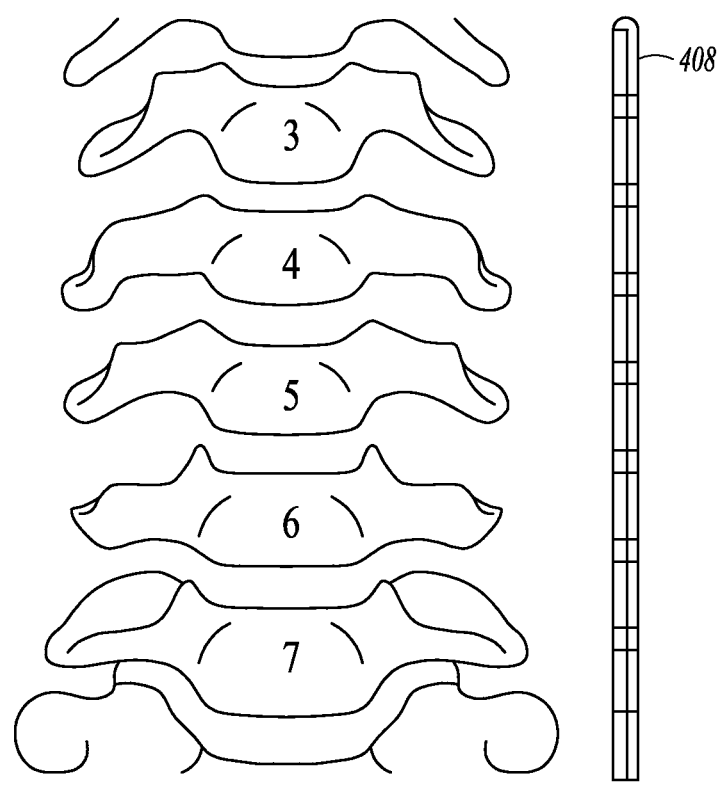
FIG. 4 shows an illustration of a multi-electrode lead for stimulating nerves of the spinal cord.

FIG. 4 shows an illustration of a multi-electrode lead 408 for stimulating nerves associated with the spinal cord. Note that the lead and electrodes are not drawn to the same scale as the spinal cord. The multi-electrode lead 408 may also be disposed in the azygos vein to stimulate nerves associated with the spinal cord. The multi-electrode lead 408 can be used to deliver neural stimulation pulses to decrease sympathetic activity in the sympathetic nerves branching from the spinal cord and to deliver neural stimulation pulses to increase sympathetic activity in the sympathetic nerves branching from the spinal cord. Other delivery sites for neural stimulation include, among others, the vena cava, and cardiac fat pads.

Note that although a specific arrangement of leads and electrodes are shown the Figures, the present methods and systems will work in a variety of configurations and with a variety of electrodes. An IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Other forms of electrodes include meshes and patches that can be applied to portions of the heart or nerves, or that can be implanted in other areas of the body to help "steer" electrical currents produced by the IMD.

There is a concern that providing NST to a patient receiving CFM therapy may introduce an electrical artifact that can be sensed by the CFM sensing circuits. For instance, in a device that provides combined AMT and CFM, the circuits to provide neural stimulation may affect sensing by the CFM sensing circuits through a common electrical ground of the device or through far field sensing of the constant current stimulus and charge restoring stimulus of AMT. Providing AMT with a separate device may affect sensing by a CFM device through far-field sensing. The sensed signal artifact may be interpreted as electrical cardiac activity and appropriate CFM therapy may not be provided.

The over-sensing of NST can be mitigated by providing the therapy only during those times when the CFM operation is scheduled (e.g., programmed) to turn off or minimize the CFM sensing function due to CFM therapy delivery. Some CFM devices may blank the sense amplifiers of the sensing circuits for a time period during and after delivery of a pace pulse, or for a period of time during and after a detected intrinsic event (e.g., a ventricular depolarization). The sense amplifiers are blanked to avoid sensing of a far field signal due to the pace pulse or intrinsic event. During this blanking period, the sense amplifiers are disabled to prevent a sensed signal from swamping the sensing circuitry (e.g., driving the sense amplifiers to a high or low rail). Blanking allows the sense amplifier circuits to more quickly resume sensing than if they were operated during the paced or intrinsic events.

CRM devices may also introduce a cross chamber refractory period in relation to a pace pulse or intrinsic event. During a refractory period, the sense amplifier is enabled, but any output from the sensing circuits is ignored by the device logic used in making CRM therapy decisions. The refractory period is to prevent far field signals from pacing pulses or intrinsic events in one heart chamber (e.g., a ventricle) from being interpreted by sensing circuits as heart activity occurring in another heart chamber (e.g., an atrium). Delivering NST only during one or both of these blanking and refractory periods may mitigate inappropriate sensing by the CFM sensing circuits and inappropriate therapy by the CFM therapy circuits.

Figure 5:
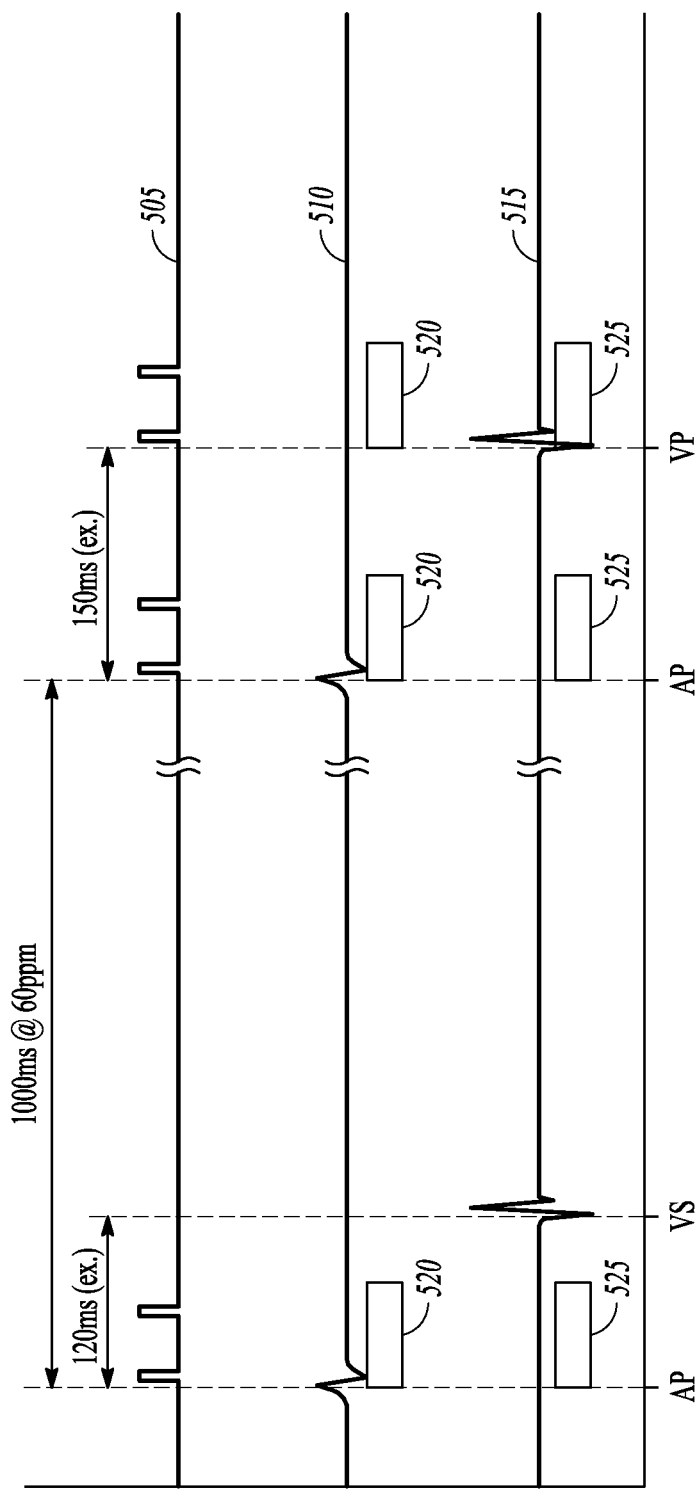
FIG. 5 is an illustration of an example of operation of a medical device.

FIG. 5 is an illustration of an example of operation of one or more medical devices. The top waveform 505 represents delivery of stimulation pulses for neural modulation therapy. The middle waveform 510 represents a filtered cardiac activity signal sensed in an atrium. The bottom waveform 515 represents a filtered cardiac activity signal sensed in a ventricle. The atrial activity shown in the middle waveform 510 is atrial depolarization resulting from providing bradycardia pacing to the atrium at 60 pulses per minute (60 ppm). A blanking period 520 is initiated in the atrial sensing channel as a result of an atrial pace (AP). Top waveform 505 shows neural stimulation pulses delivered during the atrial blanking period.

The ventricular activity shown in the bottom waveform 515 shows sensed intrinsic ventricular depolarization activity (VS) and a ventricular depolarization resulting from a pace pulse delivered to the ventricle (VP). The atrial to ventricular (A-V) time interval from the atrial pace to the ventricular sensed event is 120 milliseconds (120 ms) and the A-V interval from the atrial pace to the ventricular pace is 150 ms. Note that a ventricular blanking period 525 is not initiated after the intrinsic ventricular event (VS) so neural stimulation is not shown being delivered in the top waveform 505. A ventricular blanking period 525 is initiated after the paced ventricular event (VP) and the top waveform 505 shows neural stimulation pulses being delivered during the ventricular blanking period 525. In some examples, neural stimulation pulses are delivered only during a blanking period initiated as a result of an atrial pace. In some examples, neural stimulation pulses are delivered only during a blanking period initiated as a result of a ventricular pace. In some examples, neural stimulation pulses are delivered during both a blanking period initiated as a result of an atrial pace and a blanking period initiated as a result of a ventricular pace.

The neural stimulation pulses can be triggered by a paced event and timed to coincide with a blanking period. If the CFM functions and AMT functions are performed by one device, the device can trigger the neural stimulation in a timed relationship with a pace pulse so that the neural stimulation occurs during the blanking period. If the CFM functions and AMT functions are performed by two devices, the AMT device may include sensing circuits that are configured to sense the pacing stimulation by the CFM device and the AMT device may trigger the neural stimulation in response to a sensed pace pulse. If the CFM device and the AMT are able to communicate, the communication can be used to coordinate the CFM functions and AMT functions. The communication can be bidirectional wireless communication. In certain examples, the communication can include one or more of unidirectional communication and wired communication.

Figure 6:
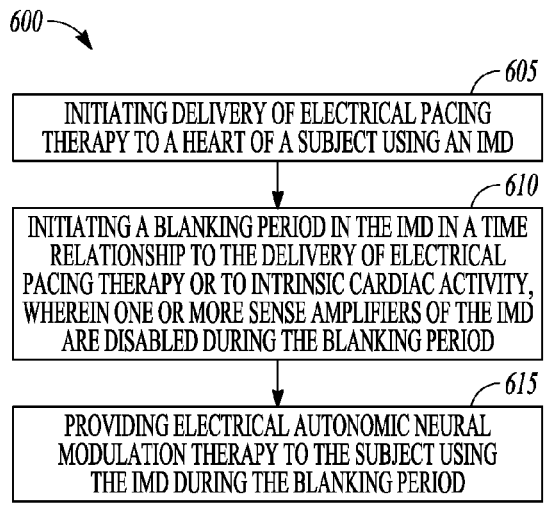
FIG. 6 shows a flow diagram of an example of a method of operating a medical device to mitigate cross therapy sensing.

FIG. 6 shows a flow diagram of an example of a method 600 of operating one or more medical devices to mitigate cross therapy sensing. At block 605, delivery of electrical pacing therapy to a heart of a subject is initiated using an IMD. At block 610, at least one of a blanking period or refractory period is initiated in the IMD in a time relationship to the delivery of electrical pacing therapy or the detection of intrinsic activity. One or more sense amplifiers of the IMD are disabled during the blanking period. At block 615, electrical neural stimulation therapy is provided to the subject using the same IMD or a separate IMD during the blanking period.

Figure 7:
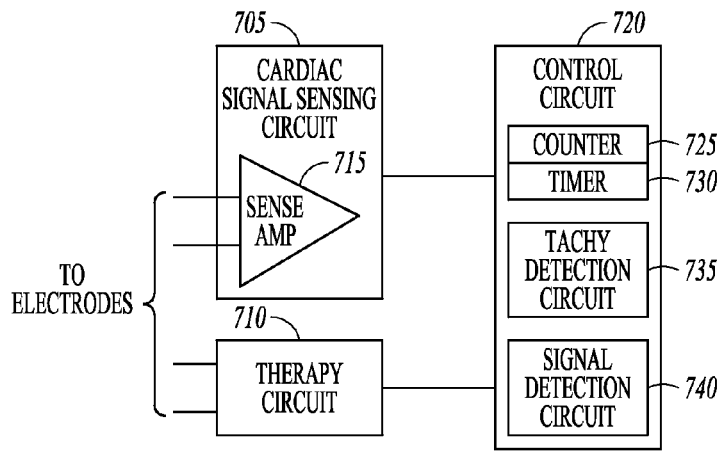
FIG. 7 shows an example of a block diagram of portions of an implantable medical device that delivers both electrical pacing therapy and electrical neural stimulation therapy and mitigates cross therapy sensing.

FIG. 7 shows an example of a block diagram of portions of an IMD that delivers both electrical pacing therapy and electrical neural stimulation therapy and mitigates cross therapy sensing. The device includes a cardiac signal sensing circuit 705 and a therapy circuit 710. The cardiac signal sensing circuit 705 is configured to sense an electrical cardiac signal from at least one of an atrium or ventricle of a heart of a subject, and includes at least one sense amplifier circuit 715. The therapy circuit 710 is configured to provide electrical pacing therapy to at least one of an atrium or ventricle of the heart. The therapy circuit 710 can be electrically coupled to electrodes configured for placement in or near the atrium or ventricle to deliver the therapy. The therapy circuit 710 is also configured to provide electrical NST to the subject.

Figure 8:
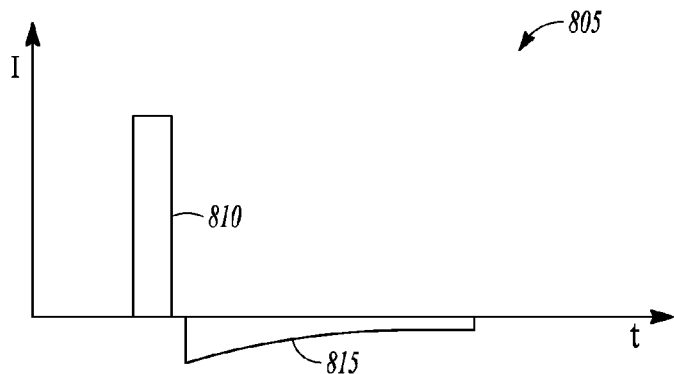
FIG. 8 shows an example of a neural stimulation pulse.

FIG. 8 shows an example of a neural stimulation pulse 805. In some examples, the neural stimulation pulse 805 can involve two portions. The first portion 810 is a current pulse of constant current amplitude. The second portion 815 includes a charge-restoring stimulus. In some examples, the amplitude of the first portion 810 is programmable.

Returning to FIG. 7, the device also includes a control circuit 720 communicatively coupled to the cardiac signal sensing circuit 705 and the therapy circuit 710. The communicative coupling allows electrical signals to be communicated between the cardiac signal sensing circuit 705, the therapy circuit 710, and the control circuit 720 even though there may be intervening circuitry. The control circuit 720 can include a processor such as a microprocessor, a digital signal processor, application specific integrated circuit (ASIC), or other type of processor, interpreting or executing instructions in software modules or firmware modules. The control circuit 720 can include other circuits or sub-circuits to perform the functions described. These circuits may include software, hardware, firmware or any combination thereof. Multiple functions can be performed in one or more of the circuits or sub-circuits as desired.

The control circuit 720 is configured (e.g., programmed) to control the neural stimulation delivered by the therapy circuit 710 according to stimulation instructions, such as a stimulation schedule stored in a memory integral to or communicatively coupled to the control circuit 720. NST can be delivered in a stimulation burst, which is a train of stimulation pulses at a predetermined frequency. Stimulation bursts can be characterized by burst durations and burst intervals. Burst duration is the length of time that a burst lasts. A burst interval can be identified by the time between the start of successive bursts. A configured pattern of bursts can include any combination of burst durations and burst intervals. A simple burst pattern with one burst duration and burst interval can continue periodically for a programmed period or can follow a more complicated schedule. The configured pattern of bursts can be composed of multiple burst durations and burst interval sequences. The configured pattern of bursts can be characterized by a duty cycle, which refers to a repeating cycle of neural stimulation ON for a fixed time and neural stimulation OFF for a fixed time. The memory may include instructions, performable by the control circuit 720, to receive therapy feedback and titrate the NST based on the feedback. One or more of the amplitude, frequency, wave morphology, burst frequency, duty cycle, and/or duration can be adjusted by the control circuit 720.

The control circuit 720 is configured to initiate delivery of the electrical pacing therapy and initiate a blanking period in a time relationship to the delivery of electrical pacing therapy. As explained previously in regard to FIG. 7, the one sense amplifier 715 or sense amplifiers are disabled during the blanking period. The control circuit 720 initiates delivery of the electrical NST to the subject during the blanking period. In some examples, the control circuit 720 selectively initiates delivery of the NST during the blanking period.

In some examples, the control circuit 720 includes a tachyarrhythmia detection circuit 735 that detects tachyarrhythmia by detecting a heart rate that satisfies a specified rate detection threshold or by detecting a heart rate interval that satisfies a specified interval threshold. The control circuit 720 may suspend or disable delivery of NST when the tachyarrhythmia detection circuit 735 detects an episode of tachyarrhythmia. The delivery of neural therapy may be disabled during one or more of a post-detection period, a post-shock period, and a specified redetection period.

In some examples, the control circuit 720 selectively initiates delivery of the NST according to a schedule. In some examples, the control circuit 720 changes the blanking period (e.g., lengthens the blanking period) when the therapy is scheduled and NST is initiated during the blanking period. Lengthening of the blanking period may be useful to further reduce cross therapy over-sensing.

In some examples, the amount of lengthening of the blanking period may be limited. For example, the time duration of the blanking period may be limited according to a specified tachyarrhythmia detection rate, or rate detection interval. For instance, lengthening of a blanking period in the ventricular channel may be limited when the blanking period is initiated as a result of a paced atrial event. This is done to allow detection of ventricular rates that may indicate tachyarrhythmia. The limiting may performed by the device or by an external device programming a variable blanking period into the implantable device.

However, under some circumstances such as a clinical setting, the medical device may be configured to delay or forego the tachyarrhythmia detection in order to meet a therapy goal. Thus, the control circuit 720 may delay tachyarrhythmia detection by the tachyarrhythmia detection circuit 735 during delivery of NST. This delay may be in response to one or more of manual enabling of the neural modulation therapy, semi-automatic enabling of the neural therapy by the device, or automatic enabling of the therapy by the device. In certain examples, tachyarrhythmia can be delayed a number of seconds (e.g., 5 sec., 10 sec., 30 sec., etc.) while the neural therapy is delivered. In certain examples, the neural therapy is duty cycled to accommodate some tachyarrhythmia detection during the neural modulation therapy. This duty cycling can include a ratio of the time that neural modulation therapy is enabled and tachyarrhythmia detection disabled to the time that NST is disabled and tachyarrhythmia detection enabled (e.g., a ratio of 0.2, 0.25, 0.33, 0.5, etc.).

Figure 9:
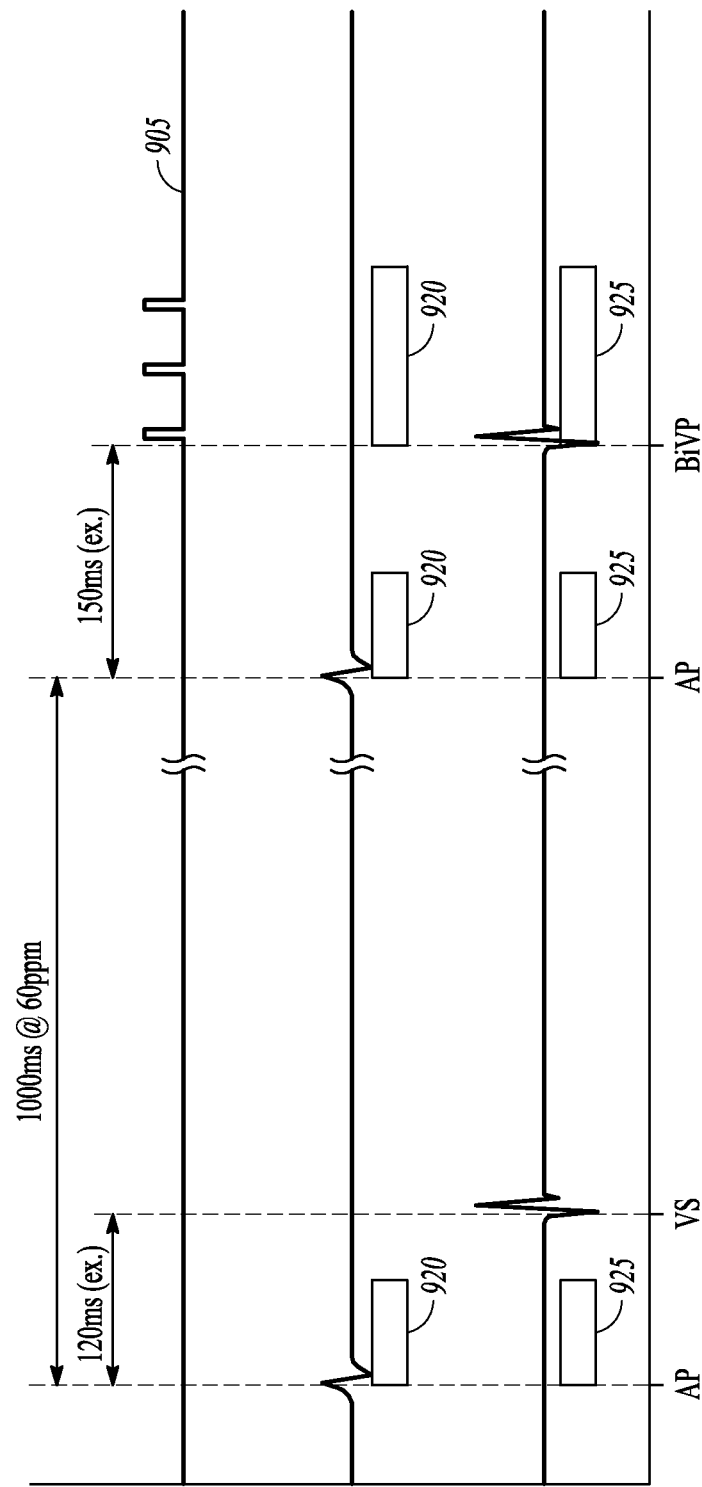
FIG. 9 is an illustration of an example of operation of a medical device that delivers bi-ventricular pacing.

According to some examples, the therapy circuit 710 provides bi-ventricular pacing therapy. FIG. 9 is another illustration of an example of operation of one or more medical devices. The illustration in FIG. 9 is similar to the illustration of the example in FIG. 5, except that bi-ventricular pacing (BiVP) is provided if no intrinsic event is sensed causing the A-V delay counter to timeout. Both ventricles of the heart are paced, and the control circuit 720 initiates a blanking period 920, 925 in a time relationship to a pace delivered as part of the bi-ventricular pacing therapy.

In some examples, the device of FIG. 7 includes an atrial sensing channel that includes a sense amplifier and at least one ventricle sensing channel that also includes a sense amplifier. The sense amplifiers are disabled during the blanking period. In some examples, the bi-ventricular blanking period can be longer than a blanking period for a single chamber ventricle pace. To take advantage of the longer blanking period, the control circuit 720 provides NST to the subject during the blanking period to take advantage of the longer bi-ventricular blanking period, as shown in waveform 905 of FIG. 9. In some examples, the delivery of NST is limited to during the bi-ventricular blanking period.

According to some examples, the control circuit 720 initiates a refractory period in a time relationship to the delivery of electrical pacing therapy. During a refractory period, the sense amplifier 715 or sense amplifiers are enabled during the refractory period but electrical signals sensed by the sense amplifiers are ignored by the device logic used in making CRM therapy decisions. The refractory period timed in the CFM device can be implemented to coincide with a refractory period of the myocardium. The refractory period of the myocardium corresponds to a time after onset of an action potential during which the myocardium cannot respond at all to either intrinsic or extrinsic stimulation.

Figure 10:
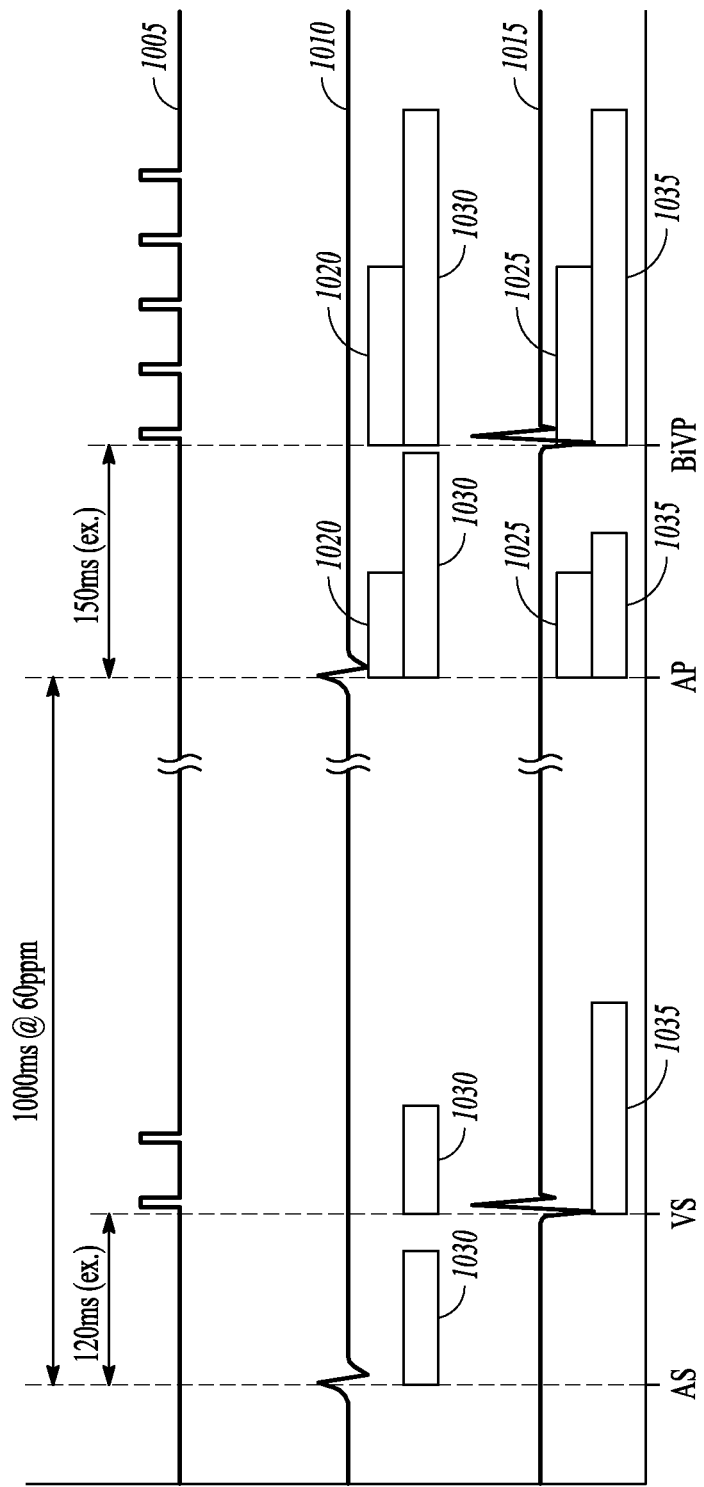
FIG. 10 shows another illustration of an example of operation of a medical device.

FIG. 10 shows another illustration of an example of operation of one or more medical devices. As in the other examples, the top waveform 1005 represents delivery of neural stimulation pulses. The middle waveform 1010 represents a filtered cardiac activity signal sensed in an atrium. The bottom waveform 1015 represents a filtered cardiac activity signal sensed in a ventricle. However, in this example the first atrial activity is a sensed intrinsic cardiac depolarization (AS) and the first ventricular depolarization is also a sensed intrinsic depolarization (VS). In the example, because there is not a paced event, the control circuit 720 does not initiate a blanking period for the intrinsic atrial and ventricular depolarizations. In the example, the control circuit 720 initiates an atrial sensing channel refractory period 1030 in response to the sensed atrial depolarization, and initiates a ventricular sensing channel refractory period 1035 in response to the intrinsic ventricular depolarization.

Waveform 1010 of the example shows an atrial paced event occurring 1000 ms after the intrinsic atrial event and waveform 1015 shows a bi-ventricular paced event following the atrial paced event. The control circuit 720 may initiate an atrial channel blanking period 1020 and a ventricular channel blanking period 1025 after the paced events. In some examples, the control circuit 720 may initiate an atrial sensing channel refractory period 1030 and a ventricular sensing channel refractory period 1035 in response to the paced events. Output from sense amplifiers of the atrial sensing channel and sense amplifiers of the ventricular is ignored during the refractory periods. The refractory periods are shown as starting at the same time as a blanking period, but this is not necessary as the sense amplifiers are disabled during the blanking period.

The control circuit 720 can selectively initiate NST to the subject during the refractory period. As shown in waveform 1005, the control circuit may initiate NST to the subject during one or both of a blanking period and a refractory period associated with a ventricular event. In some examples, the control circuit 720 may increase the refractory period when the NST is initiated during the refractory period. As with the blanking period, the device may limit the increase or lengthening of the refractory period to avoid impacting tachyarrhythmia detection.

Figure 11:
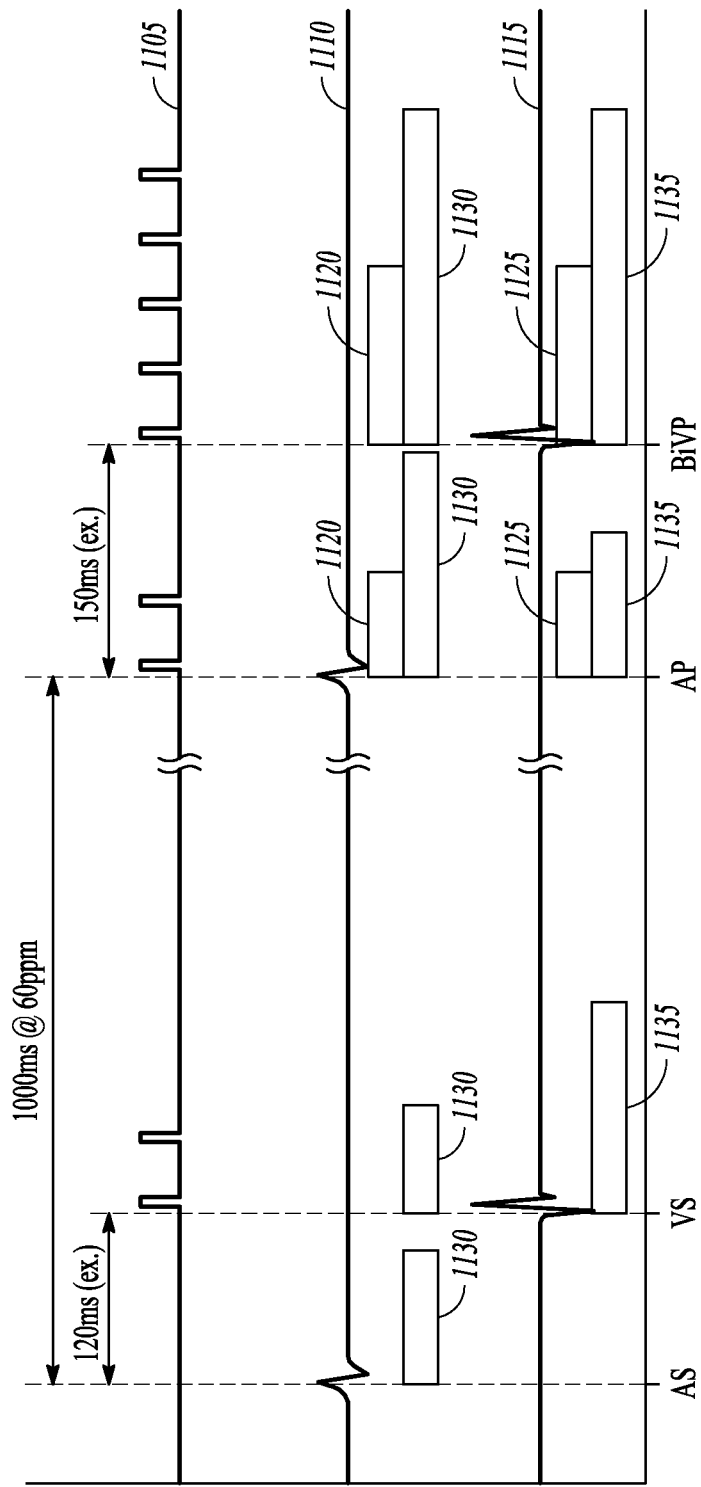
FIG. 11 shows yet another illustration of an example of operation of a medical device.

According to some examples, the control circuit 720 initiates delivery of NST during any CFM event that places all channels in blanking or in refractory. This is shown in the example of FIG. 11. As in the example of FIG. 10, the top waveform 1105 represents delivery of neural stimulation pulses. The middle waveform 1110 represents a filtered cardiac activity signal sensed in an atrium. The bottom waveform 1115 represents a filtered cardiac activity signal sensed in a ventricle. As in FIG. 10, the first CFM events are a sensed intrinsic atrial depolarization and a sensed intrinsic ventricular depolarization, and the second CFM events include a paced atrial depolarization and a paced bi-ventricular depolarization. The control circuit 720 of FIG. 7 initiates delivery of NST during the refractory periods 1130 and 1135 associated with the ventricular sensed event due to both the atrial and ventricular sensing channels being placed in refractory. The control circuit 720 also initiates NST during one or both of the blanking periods 1120, 1125 and the refractory periods 1130, 1135 associated with the atrial paced event and the ventricular paced event because both the atrial sense channel and ventricular sense channel are either blanked or in refractory. The control circuit 720 may change the time duration of one or more blanking periods and refractory periods if NST is going to be delivered during the blanking and refractory periods.

NST can be delivered according to a target dosing, such as a target number of stimulation pulses delivered per day for instance. In some examples, the control circuit 720 includes a counter circuit 725 and a timer circuit 730. The counter circuit 725 and timer circuit 730 may be integral to or communicatively coupled to the control circuit 720. The control circuit 720 tracks the number of neural stimulation therapy pulses delivered over a specified time interval using the counter circuit 725 and timer circuit 730. If neural stimulation pulses were being delivered during a blanking period, the control circuit 720 initiates additional delivery of NST during at least one subsequent blanking period to meet a specified neural modulation therapy delivery target when the number of neural stimulation therapy pulses delivered is less than the specified neural stimulation therapy delivery target. In other words, neural stimulation is delivered using subsequent blanking periods (and refractory periods) to catch up to the therapy delivery target. Some examples of a specified delivery target include a specified number of neural stimulation therapy electrical pulses delivered per hour and a specified number of neural stimulation therapy electrical pulses delivered per day.

A possible side effect of AMT is that the intrinsic rate of the subject may be driven down to the lower rate limit of the device. The lower rate limit is sometimes called the ventricular escape interval. In some examples, the control circuit 720 is configured to initiate the pacing therapy at a lower rate limit or upon expiration of a lower rate limit interval to at least one of an atrium or ventricle in the absence of intrinsic cardiac activity. To avoid driving the depolarization rate of the patient down to the lower rate limit through the AMT, the control circuit 720 suspends delivery of NST when initiating the pacing therapy within a specified range of the lower rate limit or lower rate limit interval. In certain examples, the specified range is within 5 beats per minute (bpm) of the lower rate limit, and in certain examples, the specified range is within 10 bpm of the lower rate limit.

If the control circuit 720 is tracking a number of neural stimulation therapy pulses delivered over a specified time interval to meet a specified neural modulation therapy delivery target, the control circuit 720 may only initiate any additional delivery of neural stimulation therapy to meet the specified target when the IMD is providing pacing therapy outside of the specified range of the lower rate limit or the lower rate limit interval.

According to some examples, the device provides antitachyarrhythmia pacing (ATP) therapy. ATP may first be used to try and convert a tachyarrhythmic episode to spare the patient any discomfort from high-energy shock therapy. ATP can involve bursts of pacing pulses delivered at a high rate. Because of the rates involved, there is often little sensing done by the device during delivery of ATP, and one or both of blanking periods and refractory periods can be imposed during ATP delivery. Thus, the device may initiate delivery of NST during one or both of blanking and refractory periods during ATP. As explained above, autonomic neural modulation therapy may drive down the heart rate of the subject. Providing the neural therapy with the ATP during the tachyarrhythmic episode may provide the added benefit of increasing the likelihood of success of the ATP.

The several examples described herein address the problem of cross-therapy sensing by delivering AMT only during time intervals when the CFM sensing function of the device is blanking the CFM sensing channels because of CFM therapy delivery. Another approach is to reduce the sensitivity of the CFM sensing channels during delivery of AMT stimulation pulses. Thus, the sensitivity of the CFM sensing function is reduced according to the neural stimulation timing, rather than adjusting the neural stimulation timing to wait for an opportune delivery time determined by the CFM therapy.

Figure 12:
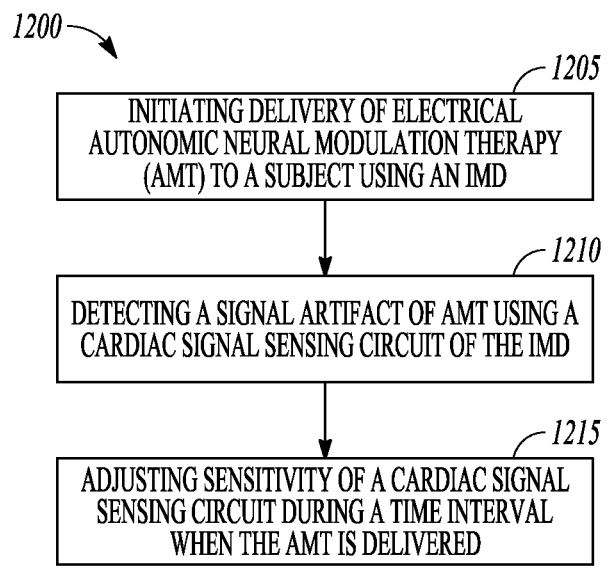
FIG. 12 shows a flow diagram of an example of a method of operating a medical device to mitigate cross therapy sensing.

FIG. 12 shows a flow diagram of an example of a method 1200 of operating one or more medical devices to mitigate cross therapy sensing. At block 1205, delivery of electrical neural stimulation therapy to a subject is initiated using an IMD. At block 1210, a signal artifact of the AMT is detected using a cardiac signal sensing circuit of the IMD. The signal artifact may be detected by sense amplifiers of one or both of an atrial sense channel and a ventricular sense channel. In some examples, the cardiac signal is filtered to detect the frequency of delivery of the neural stimulation pulses.

At block 1215, in response to detecting the signal artifact, sensitivity of a cardiac signal sensing circuit is changed during a time interval when the AMT is delivered. Changing the sensitivity of the cardiac signal sensing circuit can include one or more of changing a sensing threshold of sense amplifiers included in the cardiac signal sensing circuit, disabling operation of the sense amplifiers during delivery of the AMT, and disabling the output of the sense amplifiers.

The sensing parameters can be adjusted by a clinician in response to the device an alert from the device in response to detecting the signal artifact, or the sensing parameters can be adjusted by the medical device itself in response to detection.

According to some examples, the control circuit 720 of FIG. 7 initiates delivery of the pacing therapy and initiates the delivery of the AMT as described previously. The control circuit 720 can include a signal detection circuit 740 to detect a signal artifact of the NST in the sensed cardiac signal. In some examples, the signal detection circuit 740 includes a peak detector and is configured to recognize when a frequency of detected peaks matches a frequency with which neural stimulation pulses are delivered. In some examples, the signal detection circuit 740 includes one or more filter circuits to detect a signal at the frequency of delivery of the neural stimulation. In some examples, the filter circuits are programmable to match the frequency of delivery of stimulation pulses of the NST. In response to detecting the signal artifact, the control circuit 720 changes the sensitivity of the cardiac signal sensing circuit 705 during delivery of the NST.

Figure 13:
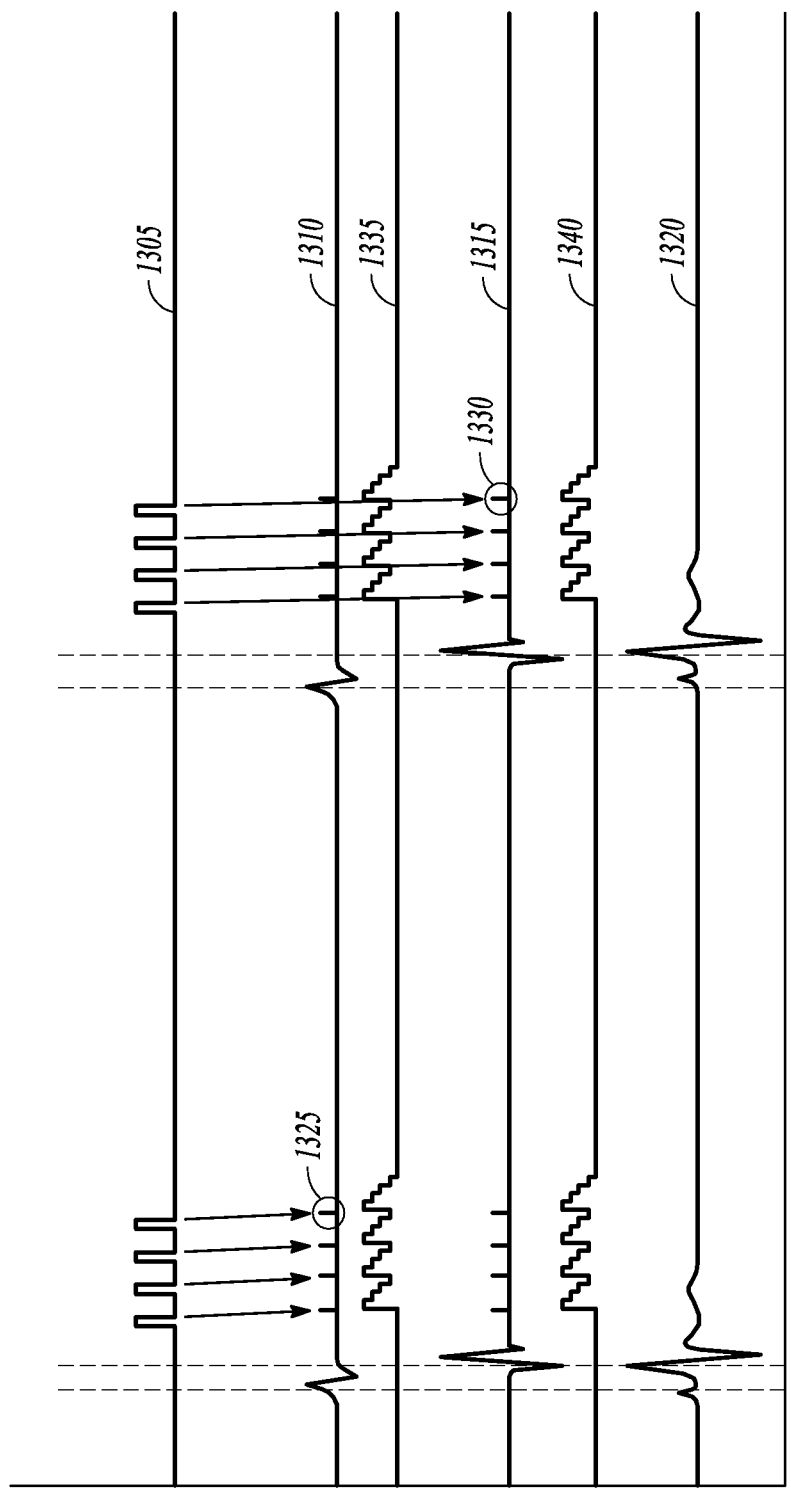
FIG. 13 is an illustration of an example of operating a medical device to mitigate cross therapy sensing by increasing a sensing threshold.

In some examples, the control circuit 720 is configured to increase a sensing threshold of the sense amplifier 715 during delivery of the NST. FIG. 13 is an illustration of an example of operation of one or more medical devices to mitigate cross therapy sensing by increasing a sensing threshold. The illustration shows six waveforms. The top waveform 1305 represents an example of delivery of stimulation pulses for NST. The example shows only four pulses to simplify the illustration. The second waveform 1310 represents a filtered cardiac activity signal sensed in an atrium. Skipping to the fourth waveform 1315, a representation of a filtered cardiac activity signal sensed in a ventricle is shown. The bottom waveform 1320 is a representation of an electrocardiogram (EKG) corresponding to the depolarization activity in the atrium and ventricle.

The arrows from the pulses in the top waveform indicate representations of artifacts 1325 in the sensed atrial cardiac signal due to NST, and representations of artifacts 1330 in the sensed ventricular signal due to NST. It should be noted that the artifacts can be present even though the sensed signals are filtered. In response to this sensing, the IMD automatically reduces the sensitivity of a sense amplifier, in one or both of the atrial sensing channel and the ventricle sensing channel, to minimize the detection. In certain examples, reducing sensitivity of a sense amplifier is accomplished by raising the input sensing threshold of the sense amplifier, so that signals sensed by the sense amplifier have larger amplitude. In certain examples, reducing sensitivity of a sense amplifier is accomplished by increasing the output dynamic range of the sense amplifier. For example, if the output dynamic range of the sense amplifier is equivalent to 0-100 mV, then the sense amplifier would sense input signals greater than 10 mV. If the output dynamic range is increased to 0-200 mV, then the sense amplifier would sense input signals greater than 20 mV.

The third waveform 1335 shows a device, such as the control circuit 720 of the device of FIG. 7, automatically changing the sensing threshold of the sense amplifier in the atrial channel to reduce sensitivity. The steps represent the threshold being increased to a high threshold to eliminate the artifact and then stepped down until the artifact reappears in the sensed signals. The sensing threshold is then increased to one step higher to eliminate the signal artifact with the lowest increase in the sensing threshold. The fifth waveform 1340 shows a similar automatic adjustment for a sense amplifier for the ventricular sensing channel. In some examples, the sensing threshold is increased in steps until the artifact is no longer sensed in the cardiac signals. In some examples, an alert is generated when the artifact appears and a user initiates the adjustment to the sensing thresholds of the amplifiers.

According to some examples, the control circuit 720 changes the sensitivity of the cardiac signal sensing circuit 705 by disabling operation of the sense amplifier 715 during delivery of the NST. This can be referred to as initiating a blanking period during delivery of the neural stimulation. In certain examples, the sense amplifiers are disabled during the blanking period by disconnecting one or both of the circuit connections to the sense amplifier and electrode connections to the sense amplifier. In certain examples, one or more sense amplifiers are powered down during the blanking period.

Figure 14:
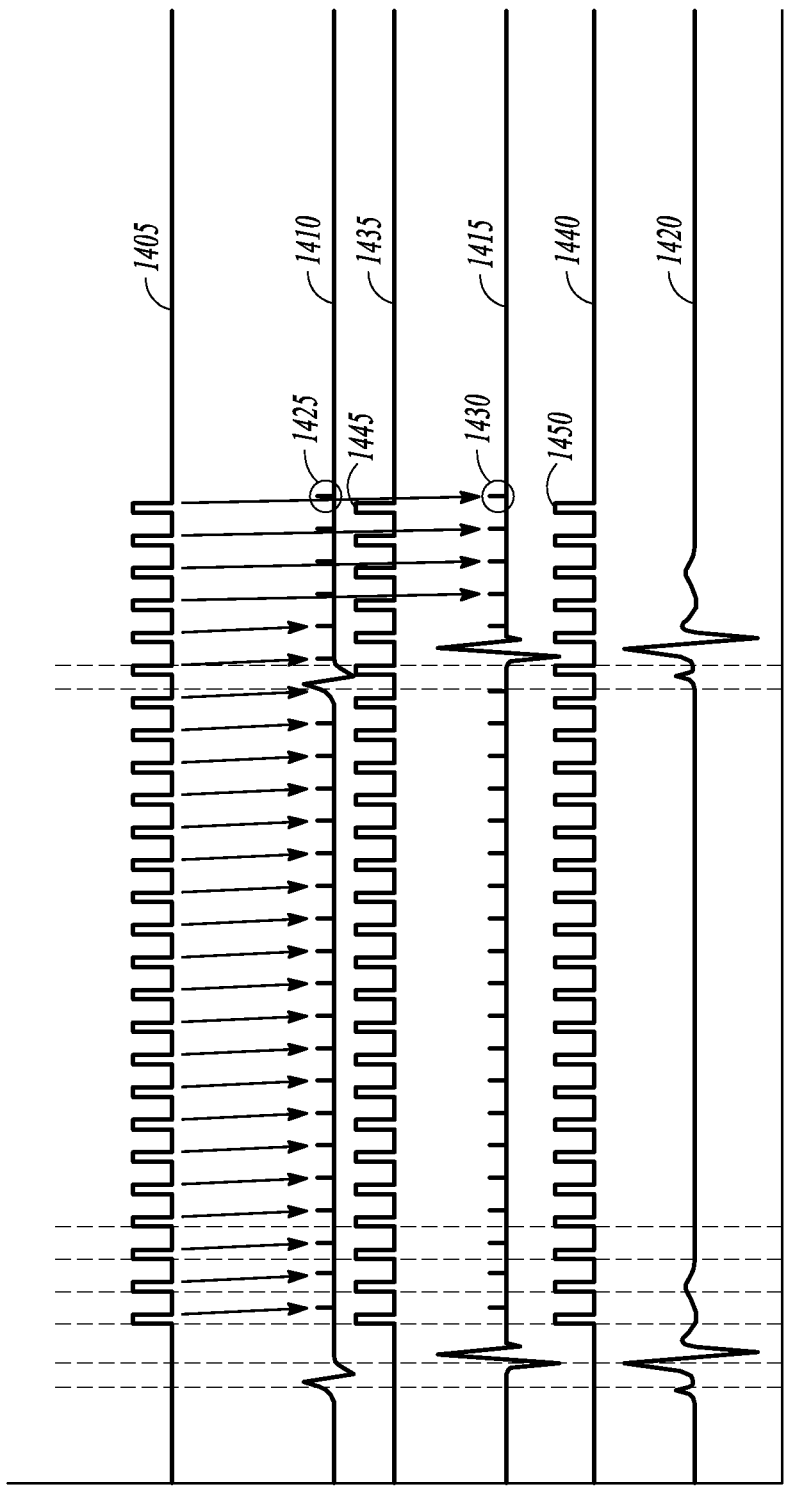
FIG. 14 is an illustration of another example of operating a medical device to mitigate cross therapy sensing.

FIG. 14 is an illustration of an example of operation of one or more medical devices (such as the IMD of FIG. 7) to mitigate cross therapy sensing by blanking one or more sense amplifiers during delivery of neural modulation therapy. As in the example of FIG. 13, the illustration of FIG. 14 shows six waveforms. The top waveform 1405 represents an example of delivery of stimulation pulses for NST. The example shows a burst of neural stimulation pulses that spans the duration of a cardiac cycle. The second waveform 1410 represents a filtered cardiac activity signal sensed in an atrium, the fourth waveform 1415 represents a filtered cardiac activity signal sensed in a ventricle, and the bottom waveform 1420 is a representation of an EKG corresponding to the depolarization activity in the atrium and ventricle.

The arrows from the stimulation pulses in the first waveform 1405 indicate signal artifacts 1425, 1430 in the sensed atrial and ventricular signals due to NST. To eliminate sensing of the artifact by the cardiac signal sensing circuit 705, the control circuit 720 of FIG. 7 initiates blanking periods when the neural stimulation pulses are provided. The third waveform 1435 shows the control circuit 720 timing a blanking period 1445 in the atrial sensing channel at the time of the neural stimulation pulse. The fourth waveform 1440 shows the control circuit 720 timing a blanking period 1450 in the ventricular sensing channel at the time of the neural stimulation pulse. In certain examples, the blanking period can begin just before the neutral stimulation pulse and lasts until just after the stimulation pulse. The blanking period may last longer to include any conduction time form the stimulation site to the sensing site. In certain examples, the blanking period is sufficient to blank the sense amplifiers during both a constant current stimulus and a charge-restoring stimulus of a neural stimulation pulse. Note that the blanking period is initiated based on the NST and not initiated according to CFM therapy.

Figure 15:
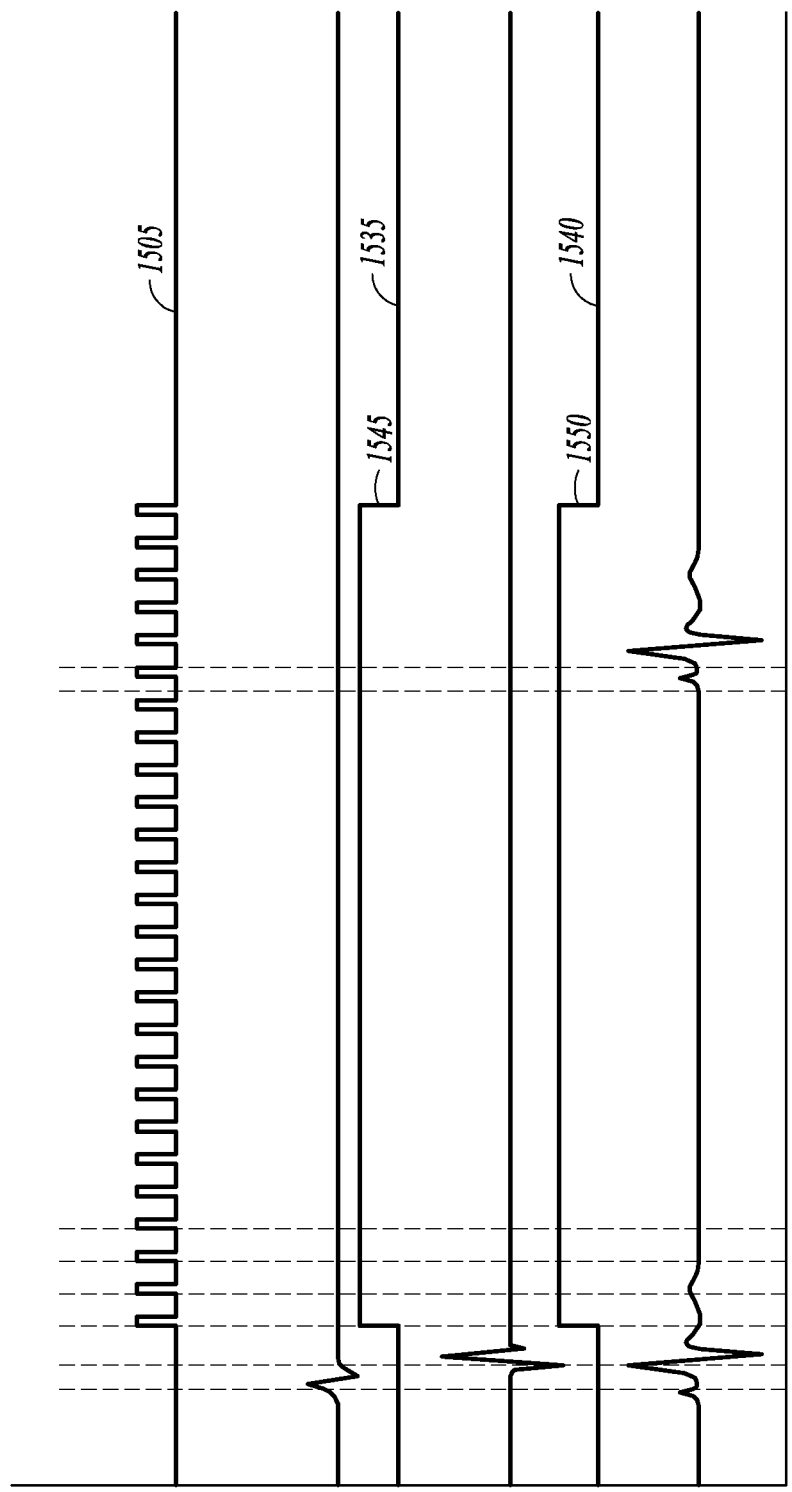
FIG. 15 is an illustration of still another example of operating a medical device to mitigate cross therapy sensing.

FIG. 15 is an illustration of another example of operation of one or more IMDs to mitigate cross therapy sensing by blanking one or more sense amplifiers. As in the examples of FIG. 13 and FIG. 14, the top waveform 1505 represents an example of delivery of stimulation pulses for NST, and the second waveform 1510 represents a filtered cardiac activity signal sensed in an atrium The third waveform 1535 shows the control circuit 720 timing a blanking period 1545 in the atrial sensing channel at the time of the neural stimulation pulse. The fourth waveform 1540 shows the control circuit 720 timing a blanking period 1550 in the ventricular sensing channel at the time of the neural stimulation pulse. The bottom waveform 1520 is a representation of an EKG corresponding to the depolarization activity in the atrium and ventricle. In the example, control circuit 720 establishes blanking periods 1545, 1550 for the entire duration of the burst of neural stimulation pulses in the top waveform 1505. This means that, for this example, sense amplifiers would be disabled during the entire burst of pulses. If the burst includes many pulses, this may reduce the ability of the IMD to detect arrhythmias. Because imposing a blanking period for an entire burst of pulses may adversely affect the ability of the tachyarrhythmia detection circuit 735 to detect rates or heart beat intervals associated with tachyarrhythmia, the operation shown in FIG. 15 may be used in, for example, a clinical setting where a patient can be monitored directly by a clinician.

Figure 16:
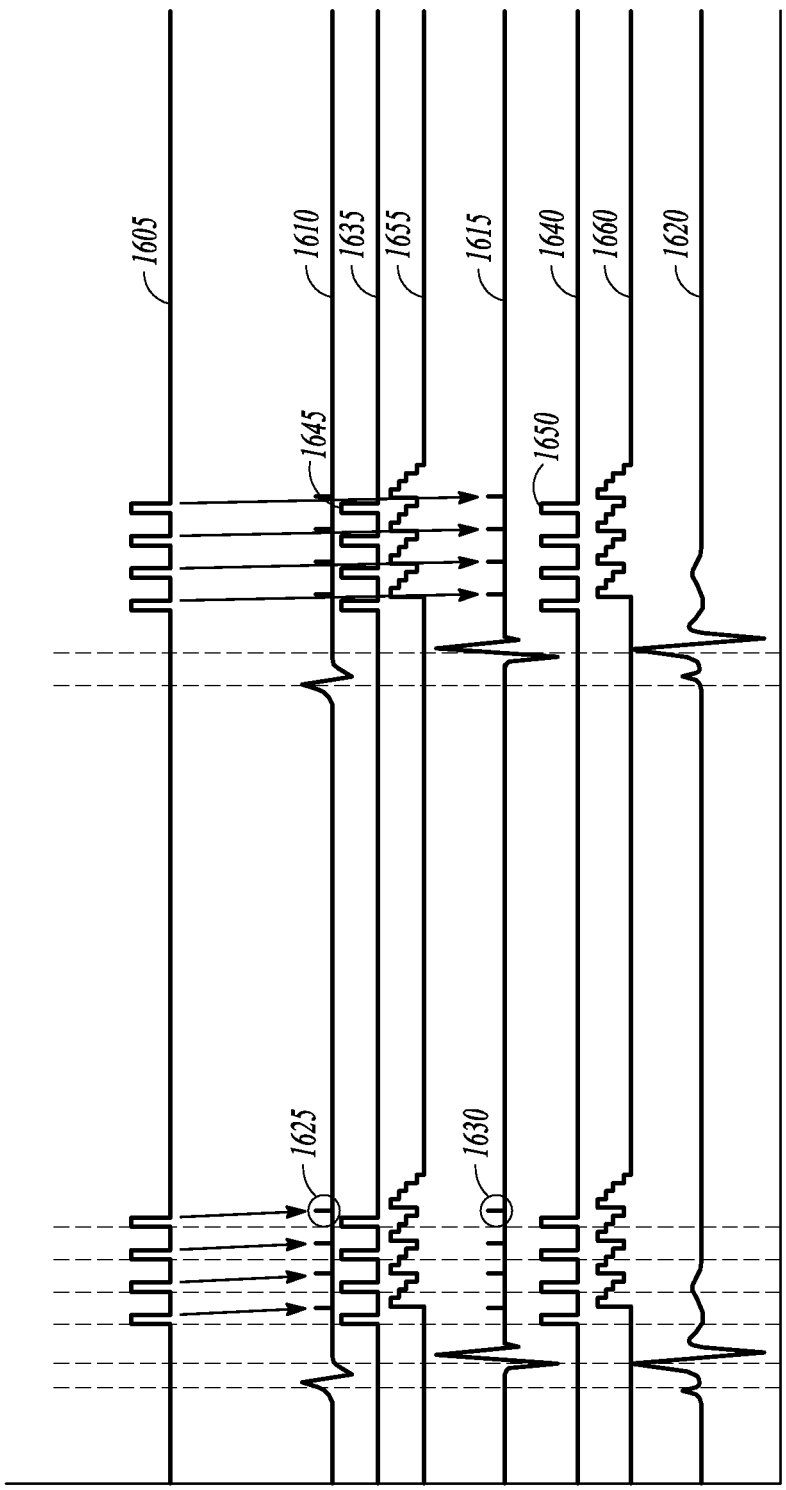
FIG. 16 is an illustration of still another example of operating a medical device to mitigate cross therapy sensing.

FIG. 16 is an illustration of still another example of operation of one or more medical devices (such as the device of FIG. 7) to mitigate cross therapy sensing. In the example, sensitivity of the cardiac signal sensing circuit 705 of FIG. 7 is changed by initiating both a blanking period and reducing the sensitivity of the sense amplifier 715. Neural stimulation pulses, shown in the top waveform 1605, result in signal artifacts from the stimulation being present in the sensed atrial signal shown in the second waveform 1610 and in the sensed ventricular channel shown in the fifth waveform 1615. The bottom waveform 1620 is a representation of an EKG corresponding to the depolarization activity in the atrium and ventricle. The control circuit 720 changes the sensitivity of the cardiac signal sensing circuit 705 by establishing blanking periods 1645, 1650 (as shown in waveforms 1635, 1640) during a constant current portion of the neural stimulating pulse by increasing the sensing threshold of one or more sense amplifiers (as shown in waveforms 1655, 1660) during the charge-restoring portion of the stimulation.

According to some examples, the control circuit 720 reduces sensitivity of the cardiac signal sensing circuit 705, by establishing a refractory period in one or more sensing channels during delivery of neural stimulation pulses. During a refractory period the output of the sense amplifiers are i ignored by the device logic used in making CRM therapy decisions. In some examples, in response to detecting the signal artifact, the control circuit 720 disables the output of the sense amplifier 715 of the cardiac signal sensing circuit 705 during the time interval when a neural stimulation pulse is delivered.

Figure 17:
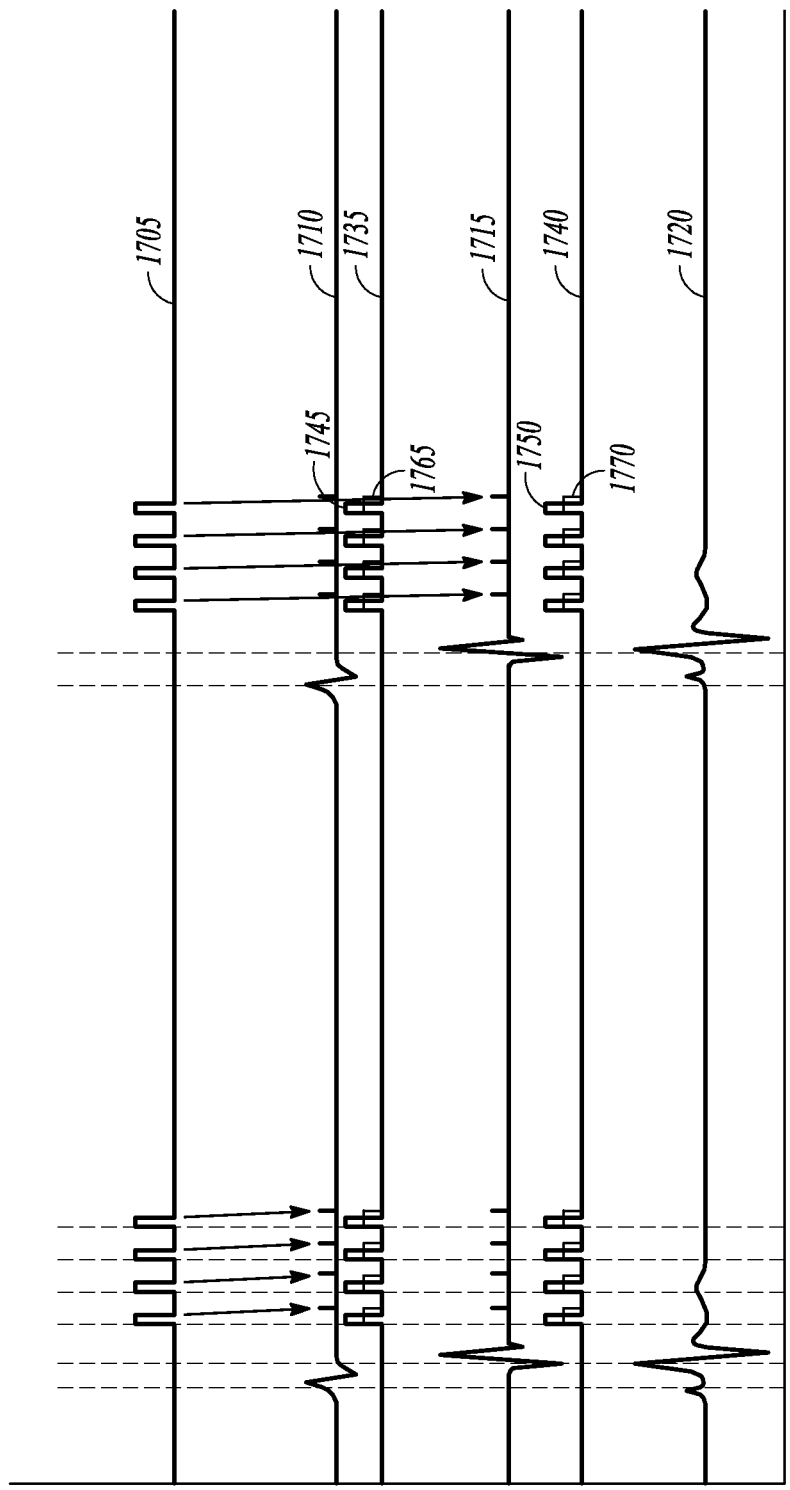
FIG. 17 is an illustration of still another example of operating a medical device to mitigate cross therapy sensing.

FIG. 17 is an illustration of still another example of operation of one or more medical devices (such as the device of FIG. 7) to mitigate cross therapy sensing. In the example, sensitivity of the cardiac signal sensing circuit 705 of FIG. 7 is changed by initiating both a blanking period and a refractory period during a neural stimulation pulse. As in the previous examples of FIGS. 13-16, neural stimulation pulses (shown in the top waveform 1705) result in signal artifacts from the stimulation being present in one or more of the sensed atrial signal shown in the second waveform 1710 and in the sensed ventricular channel shown in the fifth waveform 1715. The bottom waveform 1720 is a representation of an EKG corresponding to the depolarization activity in the atrium and ventricle. The control circuit 720 changes the sensitivity of the cardiac signal sensing circuit 705 by establishing blanking periods 1745, 1750 (as shown by waveforms 1735, 1740) and by initiating refractory period 1765, 1770. In some examples, the duration of the blanking period can cover the duration of a constant current portion of the neural stimulation, and the refractory period can cover charge-restoring portion of the neural stimulation.

The detecting of NST stimuli in sensed cardiac signals is addressed in FIGS. 5 and 9-11 by waiting until times when the sensing by the CFM sensing circuitry is minimized or disabled. In FIG. 13-17, the detecting of NST stimuli in sensed cardiac signals is addressed by changing the sensitivity of the CFM sensing circuits when delivery of NST is scheduled. The two approaches can be combined in one system (that includes one or more medical devices or systems) to address the detecting of artifacts from NST. NST may be delivered during times when the sensing by the CFM sensing circuitry is minimized or disabled and deliver NST when changing the sensitivity of a CFM sensing channel. Any of the delivery methods described herein can be combined to deliver NST and avoid cross-therapy sensing. In some examples, the control circuit 720 of FIG. 7 is configured to initiate delivery of NST stimuli during times when the sensing by the CFM sensing circuitry is minimized or disabled. The control circuit 720 may reduce the sensitivity of a sensing channel to deliver NST when further NST stimuli are needed to meet a therapy delivery schedule.

Over-sensing by a device providing multiple types of therapy to a patient may complicate the diagnostic and therapy delivery functions by such devices. Avoiding cross-therapy over-sensing will lead to improved reliability and efficacy in delivering device-based therapy to the subject.

ADDITIONAL NOTES AND EXAMPLES

Example 1 includes subject matter (such as an apparatus) comprising a cardiac signal sensing circuit, a therapy circuit, and a control circuit. The cardiac signal sensing circuit is configured to sense an electrical cardiac signal from at least one of an atrium or ventricle of a heart of a subject, and includes at least one sense amplifier circuit. The therapy circuit is configured to provide electrical pacing therapy and electrical neural stimulation therapy to the subject. The control circuit is configured to initiate delivery of the electrical pacing therapy, initiate a blanking period in a time relationship to the delivery of electrical pacing therapy (wherein the at least one sense amplifier is disabled during the blanking period), and initiate delivery of the electrical neural stimulation therapy to the subject during the blanking period.

In Example 2, the subject matter of claim 1 can optionally include the control circuit configured to selectively initiate delivery of the neural stimulation therapy during the blanking period and increase the blanking period when the neural stimulation therapy is initiated during the blanking period.

In Example 3, the subject matter of one or any combination of Examples 1-2 can optionally include the control circuit configured to initiate the pacing therapy at a lower rate limit or upon expiration of a lower rate limit interval to at least one of an atrium or ventricle in the absence of intrinsic cardiac activity, and suspend delivery of neural stimulation therapy when initiating the pacing therapy within a specified range of the lower rate limit or lower rate limit interval.

In Example 4, the subject matter of one or any combination of Examples 1-3 can optionally include a counter circuit and a timer circuit. The control circuit can optionally be configured to track a number of neural stimulation therapy pulses delivered over a specified time interval, and initiate additional delivery of neural stimulation therapy during at least one subsequent blanking period to meet a specified neural stimulation delivery target when the number of neural stimulation therapy pulses delivered is less than the specified neural stimulation delivery target.

In Example 5, the predetermined neural stimulation delivery target of Example 4 includes at least one of a specified number of neural stimulation therapy electrical pulses delivered per hour and a specified number of neural stimulation therapy electrical pulses delivered per day.

In Example 6, the subject matter of one or any combination of Examples 1-4 can optionally include the control circuit having a tachyarrhythmia detection circuit. The control circuit is configured to suspend tachyarrhythmia detection by the tachyarrhythmia detection circuit during delivery of autonomic neural modulation therapy.

In Example 7, the subject matter of one or any combination of Examples 1-6 can optionally include the control circuit having a counter circuit, and the control circuit configured to track a number of neural stimulation therapy pulses delivered over a specified time interval, and initiate additional delivery of neural stimulation therapy to meet a specified neural modulation therapy delivery target when the IMD is providing pacing therapy outside of the specified range of the at least one of the lower rate limit or the lower rate limit interval.

In Example 8, the subject matter of one or any combination of Examples 1-7 can optionally include the therapy circuit configured to provide bi-ventricular pacing therapy, and the control circuit configured to initiate a blanking period in a time relationship to a pace delivered as part of the bi-ventricular pacing therapy and limit delivery of the neural stimulation therapy to during the blanking period.

In Example 9, the subject matter of one or any combination of Examples 1-8 can optionally include the therapy circuit optionally connectable to electrodes configured to provide electrical neural stimulation therapy to at least one of a spinal cord, a vagus nerve, a location in or near an azygos vein, and one or more cardiac fat pads.

Example 10 can include subject matter (such as an apparatus), or can optionally be combined with the subject matter of one or any combination of Examples 1-9 to include such subject matter comprising a cardiac signal sensing circuit, a therapy circuit, and a control circuit. The cardiac signal sensing circuit is configured to sense an electrical cardiac signal from at least one of an atrium or ventricle of a heart of a subject, and includes at least one sense amplifier circuit. The therapy circuit configured to provide electrical pacing therapy and electrical neural stimulation therapy to the subject. The control circuit is configured to initiate delivery of the electrical pacing therapy, initiate a refractory period in a time relationship to at least one of the delivery of electrical pacing therapy or a sensed intrinsic cardiac depolarization (wherein the at least one sense amplifier is enabled during the refractory period but electrical signals sensed by the at least one sense amplifier are ignored by device logic of the IMD used in making CRM therapy decisions), selectively initiate delivery of neural stimulation therapy to the subject during the refractory period, and increase the refractory period when the neural stimulation therapy is initiated during the refractory period.

Example 11 can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter comprising initiating delivery of electrical pacing therapy to a heart of a subject using an IMD, initiating a blanking period in the IMD in a time relationship to the delivery of electrical pacing therapy, wherein one or more sense amplifiers of the IMD are disabled during the blanking period, and providing electrical neural stimulation therapy to the subject using the IMD during the blanking period.

Such subject matter can include means for initiating delivery of electrical pacing therapy to a heart of a subject using an IMD, illustrative examples of which include a control circuit or processor circuit with a therapy circuit. Such subject matter can include means for and initiating a blanking period, such as the controller circuit or processor circuit blanking one or more of a sensing channel of the IMD and a sense amplifier of the IMD. Such subject matter can include means for electrical neural stimulation therapy such as a therapy circuit connectable to electrodes configured by shape and size for placement at or near the target nerve tissue.

In Example 12, the subject matter of Example 11 can optionally include lengthening the blanking period when the autonomic neural modulation therapy is scheduled to be delivered by the IMD during the blanking period.

In Example 13, the subject matter of one or any combination of Examples 11 and 12 can optionally include limiting the lengthening of the blanking period according to a specified lowest tachyarrhythmia detection rate.

In Example 14, the subject matter of one or any combination of Examples 11-13 can optionally include tracking a number of electrical pulses delivered as part of the neural stimulation therapy over a specified time interval, and scheduling, in the IMD, additional delivery of neural stimulation therapy during one or more subsequent blanking periods to meet a predetermined neural stimulation delivery target when the number of electrical pulses delivered is less than the neural stimulation delivery target.

In Example 15, the predetermined neural stimulation therapy delivery target of Example 14 can optionally include at least one of a specified number of neural stimulation therapy electrical pulses delivered per hour and a specified number of neural modulation therapy electrical pulses delivered per day.

In Example 16, the subject matter of one or any combination of Examples 11-15 can optionally include suspending tachyarrhythmia detection by the IMD during delivery of neural stimulation therapy.

In Example 17, the subject matter of one or any combination of Examples 11-16 can optionally include establishing at least one of a lower rate limit or lower rate limit interval in the IMD, and suspending delivery of neural stimulation therapy when providing electrical pacing therapy within a specified range of the lower rate limit or lower rate limit interval.

In Example 18, the subject matter of one or any combination of Examples 11-17 can optionally include establishing at least one of a lower rate limit or lower rate limit interval in the IMD, tracking a number of electrical pulses delivered as part of the neural stimulation therapy over a second time interval, and scheduling, in the IMD, additional delivery of neural stimulation therapy to meet a predetermined neural stimulation therapy delivery target when the IMD is providing pacing therapy outside of the specified range of the at least one of the lower rate limit or the lower rate limit interval.

In Example 19, the subject matter of one or any combination of Examples 11-18 can optionally include initiating delivery of bi-ventricular pacing therapy, initiating a blanking period in a time relationship to a pace delivered as part of the bi-ventricular pacing therapy, and limiting delivery of neural stimulation therapy to during the blanking period.

Example 20 can include subject matter (such as a method, a means for performing acts, or a machine-readable medium including instructions that, when performed by the machine, cause the machine to perform acts), or can optionally be combined with the subject matter of one or any combination of Examples 1-19 to include such subject matter comprising initiating delivery of electrical pacing therapy to a heart of a subject using an implantable medical device (IMD), initiating a refractory period in the IMD in a time relationship to the delivery of electrical pacing therapy, wherein one or more sense amplifiers are enabled during the refractory period but electrical signals sensed by the one or more amplifiers are ignored by the IMD, and providing neural stimulation therapy to the subject during the refractory period. Initiating a refractory period can optionally include initiating a first refractory period of a first time duration when neural stimulation therapy is not scheduled to be delivered by the IMD during the refractory period and initiating a second refractory period of a second time duration when neural stimulation therapy is scheduled to be delivered by the IMD during the refractory period.

Such subject matter can include means for initiating delivery of electrical pacing therapy to a heart of a subject using an IMD, illustrative examples of which include a control circuit or processor circuit with a therapy circuit. Such subject matter can include means for and initiating a refractory period, such as the controller circuit or processor circuit blanking one or more of a sensing channel of the IMD and a sense amplifier of the IMD. Such subject matter can include means for electrical neural stimulation therapy such as a therapy circuit connectable to electrodes configured by shape and size for placement at or near the target nerve tissue.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." Also, in the following claims, the terms "including" and "comprising" are open-ended, that is, a system, device, article, or process that includes elements in addition to those listed after such a term in a claim are still deemed to fall within the scope of that claim.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a cardiac signal sensing circuit configured to sense an electrical cardiac signal from at least one of an atrium or ventricle of a heart of a subject, wherein the cardiac signal sensing circuit includes at least one sense amplifier circuit:
   a therapy circuit configured to provide electrical pacing therapy and electrical neural stimulation therapy to the subject; and
   a control circuit communicatively coupled to the cardiac signal sensing circuit and the therapy circuit and configured to:
   initiate delivery of the electrical pacing therapy;
   Initiate a blanking period in response to and in a time relationship to the delivery of electrical pacing therapy, wherein the at least one sense amplifier circuit is disabled during the blanking period; and
   selectively initiate delivery of the electrical neural stimulation therapy to the subject during the blanking period and increase the blanking period when the neural stimulation therapy is initiated during the blanking period.

2. An apparatus comprising:
a cardiac signal sensing circuit configured to sense an electrical cardiac signal from at least one of an atrium or ventricle of a heart of a subject, wherein the cardiac signal sensing circuit includes at least one sense amplifier circuit;
a therapy circuit configured to provide electrical pacing therapy and electrical neural stimulation therapy to the subject; and
a control circuit communicatively coupled to the cardiac signal sensing circuit and the therapy circuit and configured to:
  initiate delivery of electrical pacing therapy;
  initiate a blanking period in response to and in a time relationship to the delivery of electrical pacing therapy the at least one sense amplifier circuit is disabled during the blanking period;
  initiate delivery of the electrical neural stimulation therapy to the subject during the blanking period; and
  suspend delivery of neural stimulation therapy when the delivery of electrical pacing therapy is initiated within a specified time duration prior to the expiration of a ventricular escape interval.

3. An apparatus comprising:
a cardiac signal sensing circuit configured to sense an electrical cardiac signal from at least one of an atrium or ventricle of a heart of a subject, wherein the cardiac signal sensing circuit includes at least one sense amplifier circuit;
a therapy circuit configured to provide electrical pacing therapy and electrical neural stimulation therapy to the subject; and
a control circuit communicatively coupled to the cardiac signal sensing circuit and the therapy circuit, wherein the control circuit includes a counter circuit and a timer circuit, wherein the control circuit is configured to:
  initiate delivery of the electrical pacing therapy;
  initiate a blanking period in response to and in a time relationship to the delivery of electrical pacing therapy, wherein the at least one sense amplifier circuit is disabled during the blanking period;
  initiate delivery of the electrical neural stimulation therapy to the subject during the blanking period;
  track a number of neural stimulation therapy pulses delivered over a specified time interval; and
  initiate additional delivery of neural stimulation therapy during at least one subsequent blanking period initiated by the control circuit to meet a specified neural stimulation therapy target dosing of electrical pulses delivered within a duration of time when the number of neural stimulation therapy pulses delivered is less than the specified neural stimulation therapy target dosing.

4. The apparatus of claim 3, wherein the specified neural stimulation therapy delivery target includes at least one of a specified number of neural stimulation therapy electrical pulses delivered per hour and a specified number of neural stimulation therapy electrical pulses delivered per day.

5. The apparatus of claim 1, wherein the control circuit includes a tachyarrhythmia detection circuit, and wherein the control circuit is configured to suspend tachyarrhythmia detection by the tachyarrhythmia detection circuit during delivery of neural stimulation therapy.

6. The apparatus of claim 1, wherein the control circuit includes a counter circuit and is configured to:
  track a number of neural stimulation therapy pulses delivered over a specified time interval; and
  initiate additional delivery of neural stimulation therapy to meet a specified neural stimulation therapy delivery target when the therapy circuit is providing pacing therapy outside of the specified range of the at least one of a lower rate limit or a lower rate limit interval.

7. The apparatus of claim 1,
wherein the therapy circuit is configured to provide bi-ventricular pacing therapy, and
wherein the control circuit is configured to:
  initiate a blanking period in a time relationship to a pace delivered as part of the hi-ventricular pacing therapy; and
  limit delivery of neural stimulation therapy to during the blanking period initiated in the time relationship to the pace delivered as part of the bi-ventricular pacing therapy.

8. The apparatus of claim 1, wherein the therapy circuit is connectable to electrodes configured to provide electrical neural stimulation therapy to at least one of:
  a spinal cord;
  a vagus nerve;
  a baroreceptor;
  a location in or near an azygos vein;
  a location near the vena cava; or
  one or more cardiac fat pads.

* * * * *